United States Patent [19]

Lesher et al.

[11] 4,004,012

[45] Jan. 18, 1977

[54] 3-CYANO-5-(PYRIDINYL)-2(1H)-PYRIDINONES

[75] Inventors: George Y. Lesher, East Greenbush; Chester Joseph Opalka, Schodack, both of N.Y.

[73] Assignee: Sterling Drug Inc., New York, N.Y.

[22] Filed: Oct. 14, 1975

[21] Appl. No.: 621,763

[52] U.S. Cl. .......................... 424/263; 260/294.9; 260/295.5 A; 260/295.5 C; 260/296 D; 260/295 AM

[51] Int. Cl.$^2$ ............. A61K 31/395; C07D 213/57

[58] Field of Search ................. 260/294.9; 424/263

[56] References Cited

UNITED STATES PATENTS 3,814,771  6/1974  Shen et al. .................. 260/293.73
3,853,896  12/1974  Pessolano et al. ............. 260/296 R Primary Examiner—Alan L. Rotman
Attorney, Agent, or Firm—Robert K. Bair; B. Woodrow Wyatt

[57] ABSTRACT

Compounds useful as cardiotonic agents are 1-R-3-Q-5-PY-2(1H)-pyridinones (I) where R is hydrogen, lower-alkyl or lower-hydroxyalkyl, Q is amino (preferred) or NHAc, Ac is lower-alkanoyl or lower-carbalkoxy, and PY is 4- or 3- or 2-pyridinyl or 4- or 3- or 2-pyridinyl having one or two lower-alkyl substituents. The corresponding compounds where Q is nitro, carbamyl, cyano or hydrogen are useful as intermediates and those where Q is hydrogen or cyano also are useful as cardiotonic agents. Said compounds are prepared: by reacting $\alpha$-PY-$\beta$-(R$_1$R$_2$N)acrolein (II) with malonamide to produce 1,2-dihydro-2-oxo-5-PY-nicotinamide (Ia) and reacting Ia with a reagent capable of converting carbamyl to amino to produce 3-amino-5-PY-2(1H)-pyridone (Ib); by reacting II or $\alpha$-PY-malonaldehyde (II') with $\alpha$-cyanoacetamide to produce 1,2-dihydro-2-oxo-5-PY-nicotinonitrile (III) and partially hydrolyzing III to produce Ia; and, by heating 1,2-dihydro-2-oxo-5-PY-nicotinic acid (IV) with a mixture of concentrated sulfuric acid and concentrated nitric acid to produce 3-nitro-5-PY-2(1H)-pyridinone (Ic) and then either reducing Ic to produce Ib or first reacting Ic with an alkylating agent to produce 1-R'-3-nitro-5-PY-2(1H)-pyridinone (Id) and reducing Id to produce 1-R'-3-amino-5-PY-2(1H)-pyridinone (Ib) where R' is lower-alkyl or lower-hydroxyalkyl.

5 Claims, No Drawings

3-CYANO-5-(PYRIDINYL)-2(1H)-PYRIDINONES

BACKGROUND OF THE INVENTION a. Field of the Invention

This invention relates to 3-amino-5-(pyridinyl)-2(1H)-pyridinones, useful as cardiotonic agents, to their preparation and to intermediates used therein.

b. Description of the Prior Art

There is no teaching in the prior art of any cardiotonically active compounds having any chemical structure comparable to or suggestive of the instantly claimed compounds.

The Lesher and Gruett British Pat. No. 1,322,318, published July 4, 1973, discloses as intermediates 1,2-dihydro-2-oxo-6-(4- or 3-pyridinyl)-nicotinonitrile, 6-(4-or 3-pyridinyl)-2(1H)-pyridinone and 6-(4- or 3-pyridinyl)-2-pyridinamine.

The Brundage and Lesher U.S. Pat. No. 3,838,156, issued Sept. 24, 1974, discloses as intermediates 1,2-dihydro-2-oxo-6-Q'''-nicotinic acids where Q''' is 4(or 3)-pyridinyl or 4(or 3)-pyridinyl having one or two lower-alkyl substituents.

The Shionogi and Co. Japanese Pat. No. 20,295/67, published Oct. 11, 1967, shows 1-(x'-amino-2'-pyridinyl)-2-pyridinones as having "analgesic and antiphlogistic activity". Specifically shown is 1-(5'-amino-2'-pyridinyl)-2-pyridinone.

SUMMARY OF THE INVENTION

In a composition aspect, the invention relates to 1-R-3-Q-5-PY-2(1H)-pyridinones where R is hydrogen, lower-alkyl or lower-hydroxyalkyl, Q is nitro, carbamyl, amino or NHAc where Ac is lower-alkanoyl or lower-carbalkoxy, and PY is 4- or 3- or 2-pyridinyl or 4- or 3- or 2-pyridinyl having one or two lower-alkyl substituents. The compound where Q is amino or NHAc are useful as cardiotonic agents and those where Q is nitro or carbamyl are useful as intermediates in the preparation of the compounds where Q is amino.

Another composition aspect of the invention relates to 3-Q-5-PY-2(1H)-pyridinones where Q is hydrogen or cyano and PY is defined as above. These compounds not only are useful as intermediates in preparing the corresponding compounds where Q is amino, but also they surprisingly have been found to have useful cardiotonic activity; and, further, these compounds where Q is hydrogen surprisingly have been found to have useful bronchodilator activity.

The invention in a process aspect resides in the process of producing 3-amino-5-PY-2(1H)-pyridinone (Ib) which comprises reacting α-PY-β-($R_1R_2N$)acrolein (II) with malonamide to produce 1,2-dihydro-2-oxo-5-PY-nicotinamide (Ia) and reacting Ia with a reagent capable of converting carbamyl to amino to produce Ib, where PY is defined as above, and $R_1$ and $R_2$ are each lower-alkyl.

In another process aspect the invention comprises reacting either α-PY-β-($R_1R_2N$)acrolein (II) or α-PY-malonaldehyde (II') with α-cyanoacetamide (III) to produce 1,2-dihydro-2-oxo-5-PY-nicotinonitrile (III) and partially hydrolyzing III to produce 1,2-dihydro-2-oxo-5-PY-nicotinamide (Ia), where PY, $R_1$ and $R_2$ are each defined as above.

In another process aspect the invention comprises first heating 1,2-dihydro-2-oxo-5-PY-nicotinic acid (IV) with a mixture of concentrated sulfuric acid and concentrated nitric acid to produce 3-nitro-5-PY-2(1H)-pyridinone (Ic) and then either reducing Ic to produce 3-amino-5-PY-2-(1H)-pyridinone (Ib) or first reacting Ic with an alkylating agent of the formula R'-An to produce 1-R'-3-nitro-5-PY-2(1H)-pyridinone (Id) and reducing Id to produce 1-R'-3-amino-5-PY-2(1H)-pyridinone, where PY has the meaning given above, R' is lower-alkyl or lower-hydroxyalkyl and An is an anion of a strong inorganic acid or an organic sulfonic acid.

In another process aspect the invention comprises reacting 1-R-3-amino-5-PY-2(1H)-pyridinone with a lower-alkanoylating agent or lower-carbalkoxylating agent to produce 1-R-3-Q'-5-PY-2(1H)-pyridinone (Ie), where PY and R have the meanings given hereinabove and Q' is NHAc where Ac is lower-alkanoyl or lower-carbalkoxy, respectively.

Another composition aspect of the invention relates to a cardiotonic composition for increasing cardiac contractility, said composition comprising a pharmaceutically-acceptable carrier and, as the active component thereof, a cardiotonic 1-R-3-Q-5-PY-2(1H)-pyridinone where PY and R are defined as above and Q is cyano, hydrogen, amino or NHAc where Ac is lower-alkanoyl or lower-carbalkoxy, or pharmaceutically-acceptable acid-addition salt thereof where Q is amino.

In a method aspect, the invention relates to a method for increasing cardiac contractility which comprises the administration of a medicament comprising a pharmaceutically-acceptable carrier and, as the active component thereof, a cardiotonic 1-R-3-Q-5-PY-2(1H)-pyridinone where PY and R are defined as above and Q is cyano, hydrogen, amino or NHAc where Ac is lower-alkanoyl or lower-carbalkoxy, or pharmaceutically-acceptable acid-addition salt thereof where Q is amino.

DETAILED DESCRIPTION INCLUSIVE OF PREFERRED EMBODIMENTS

In a composition aspect the invention resides in the compounds having formula I

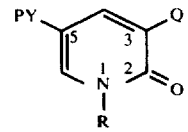

where PY is 4- or 3- or 2-pyridinyl or 4- or 3- or 2-pyridinyl having one or two lower-alkyl substituents, R is hydrogen, lower-alkyl or lower-hydroxyalkyl, and Q is nitro, carbamyl, amino or NHAc where Ac is lower-alkanoyl or lower-carbalkoxy. The compound of formula I where Q is amino or NHAc are useful as cardiotonic agents, as determined by standard pharmacological evaluation procedures. The compound of formula I where Q is nitro or carbamyl are useful as intermediates for preparing the said compounds where Q is amino. Preferred embodiments are those of formula I where Q is amino, R is hydrogen and PY is 4-pyridinyl or 3-pyridinyl. A particularly preferred embodiment is 3-amino-5-(4-pyridinyl)-2(1H)-pyridinone.

Other composition aspects resides in the compounds having formula I where R is hydrogen and Q is hydrogen or cyano. These compounds not only are useful as intermediates for preparing the compounds of formula I where Q is amino, but also are useful as cardiotonic agents and, also, where Q is hydrogen, are useful as bronchodilators, as determined by standard pharmacological procedures.

In a process aspect the invention resides in the process of producing 3-amino-5-PY-2(1H)-pyridinone (Ib) which comprises reacting α-PY-β-(R₁R₂N)acrolein (II) with malonamide to produce 1,2-dihydro-2-oxo-5-PY-nicotinamide (Ia) and reacting 1,2-dihydro-2-oxo-5-PY-nicotinamide (Ia) with a reagent capable of converting carbamyl to amino to produce 3-amino-5-PY-2(1H)-pyridinone (Ib), where PY is defined as in I above, and R₁ and R₂ are each lower-alkyl, preferably methyl or ethyl. Other process aspects of the invention reside in each of two said steps, that is, the preparation of Ia from II and the conversion of Ia to Ib.

In another process aspect the invention resides in the process of reacting either α-PY-β-(R₁R₂N)acrolein (II) or α-PY-malonaldehyde (II') with α-cyanoacetamide to produce 1,2-dihydro-2-oxo-5-PY-nicotinonitrile (III) and partially hydrolyzing 1,2-dihydro-2-oxo-5-PY-nicotinonitrile (III) to produce 1,2-dihydro-2-oxo-5-PY-nicotinamide (Ia), where PY is defined as in I above, and R₁ and R₂ are each lower-alkyl, preferably methyl or ethyl.

In another process aspect the invention resides in the process of producing 3-amino-1-R-5-PY-2(1H)-pyridinone (Ib) which comprises first heating 1,2-dihydro-2-oxo-5-PY-nicotinic acid (IV) with a mixture of concentrated sulfuric acid and concentrated nitric acid to produce 3-nitro-5-PY-2(1H)-pyridinone (Ic) and then either reducing 3-nitro-5-PY-2(1H)-pyridinone (Ic) to produce 3-amino-5-PY-2(1H)-pyridinone (Ib) or first reacting 3-nitro-5-PY-2(1H)-pyridinone (Ic) with an alkylating agent of the formula R'-An to produce 1-R'-3-nitro-5-PY-2(1H)-pyridinone (Id) and reducing 1-R'-3-nitro-5-PY-2(1H)-pyridinone (Id) to produce 1-R'-3-amino-5-PY-2(1H)-pyridinone (Ib), where R and PY have the same meanings given hereinabove for formula I, and R' is lower-alkyl or lower-hydroxyalkyl and An is an anion of a strong inorganic acid or an organic sulfonic acid. Other process aspects of the invention reside in the conversion of IV to Ic and in the two-step conversion of IV to Ic to Id.

The above process aspects of the invention are illustrated by the following flow sheet which also shows the conversion of 1,2-dihydro-2-oxo-5-PY-nicotinonitrile (III) to 1,2-dihydro-2-oxo-5-PY-nicotinic acid (IV) by hydrolysis with aqueous sulfuric acid:

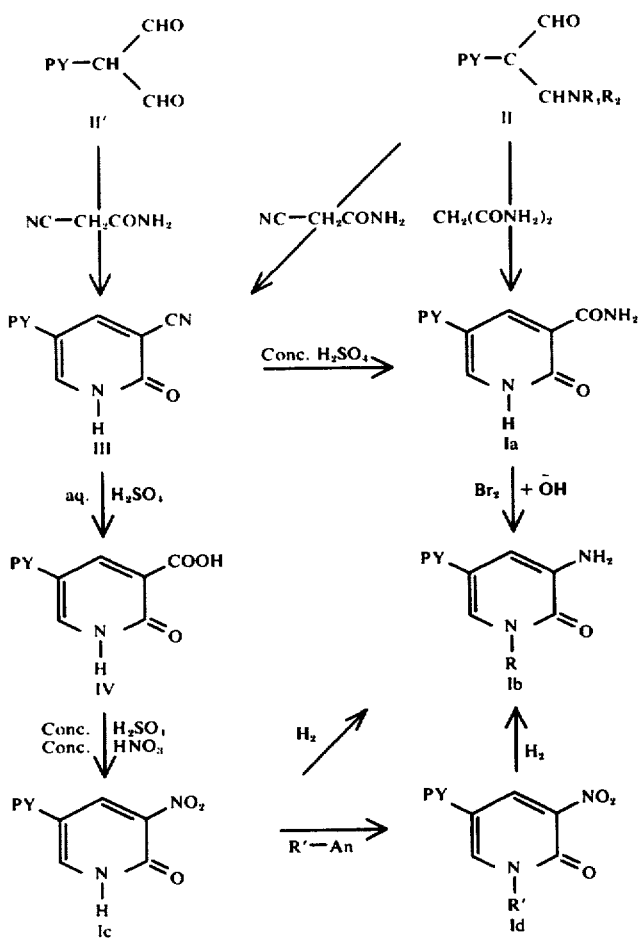

Alternatively, 1,2-dihydro-2-oxo-5-PY-nicotinonitrile (III) is converted to 3-nitro-5-PY-2(1H)-pyridinone (Ic) via 5-PY-2(1H)-pyridinone (Ie) by first refluxing III with aqueous sulfuric acid to produce 1,2-dihydro-2-oxo-5-PY-nicotinic acid (IV) and then refluxing IV in solution (without isolation) to produce Ie which is then heated with a mixture of concentrated sulfuric acid and concentrated nitric acid to produce Ic.

In another process aspect the invention resides in the process of producing 1-R-3-Q'-5-PY-2(1H)-pyridinone (Ie) which comprises reacting 1-R-3-amino-5-PY-2(1H)-pyridinone (Ib) with a lower-alkanoylating agent or lower-carbalkoxylating agent, where PY and R have the meanings given hereinabove for the compounds of formula I and Q' is NHAc where Ac is lower-alkanoyl or lower-carbalkoxy, respectively.

Another composition aspect of the invention resides in a cardiotonic composition for increasing cardiac contractility, said composition comprising a pharmaceutically-acceptable carrier and, as the active component thereof, a cardiotonic 1-R-3-Q-5-PY-2(1H)-pyridinone having the formula of claim 1 where PY and R are each defined as in formula I and Q is cyano, hydrogen, amino or NHAc where Ac is lower-alkanoyl or lower-carbalkoxy, or pharmaceutically-acceptable acid-addition salt thereof where Q is amino.

A method aspect of the invention resides in the method for increasing cardiac contractility in a patient requiring such treatment which comprises administering to such patient an effective amount of a cardiotonic 1-R-3-Q-5-PY-2(1H)-pyridinone having the formula of claim 1 where PY and R are each defined as in formula I and Q is cyano, hydrogen, amino or NHAc where Ac is lower-alkanoyl or lower-carbalkoxy, or pharmaceutically-acceptable acid-addition salt thereof where Q is amino.

The term "lower-alkyl" as used herein, e.g., as one of the meaning for R or as a substituent for PY in formula I, means alkyl radicals having from one to six carbon atoms which can be arranged as straight or branched chains, illustrated by methyl, ethyl, n-propyl, isopropyl, n-butyl, sec.-butyl, tert.-butyl, isobutyl, n-amyl, n-hexyl, and the like.

The term "lower-hydroxyalkyl", as used herein, e.g., as one of the meaning for R in formula I, means hydroxyalkyl radicals having from two to six carbon atoms and having its hydroxy group and its free valence bond (or connecting linkage) on different carbon atoms, illustrated by 2-hydroxyethyl, 2-hydroxypropyl, 3-hydroxypropyl, 2-hydroxy-2-methylpropyl, 3-hydroxypropyl, 2-hydroxy-1,1-dimethylethyl, 4-hydroxybutyl, 5-hydroxyamyl, 6-hydroxyhexyl, and the like.

Illustrative of PY in formula I where PY is 4-, 3-or 2-pyridinyl having one or two lower-alkyl substituents are the following [note that "pyridinyl" as used herein is the same as "pyridyl", the former now being the preferred term used in Chemical Abstracts]:2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl) 4-methyl-2-pyridinyl, 6-methyl-2-pyridinyl, 2,3-dimethyl-4-pyridinyl, 2,6-dimethyl-4-pyridinyl, 4,6-dimethyl-2-pyridinyl, 2-ethyl-4-pyridinyl, 2-isopropyl-4-pyridinyl, 2-n-butyl-4-pyridinyl, 2-n-butyl-4-pyridinyl, 2-n-hexyl-4-pyridinyl, 2,6-diethyl-4-pyridinyl, 2,6-diethyl-3-pyridinyl, 2,6-diisopropyl-4-pyridinyl, 2,6-di-n-hexyl-4-pyridinyl, and the like.

The term "lower-alkanoyl", as used herein, e.g., as one of the meanings for Ac in formula I, means alkanoyl radicals having from two to six carbon atoms, including the straight- and branch-chained radicals, illustrated by acetyl, propionyl (N-propanoyl), butyryl (n-butanoyl), isobutyryl (2-methyl-n-propanoyl) and caproyl (n-hexanoyl).

The term "lower-carbalkoxy", as used herein, e.g., as one of the meaning for Ac in formula I, means carbalkoxy radicals where the alkoxy portion can be straight- or branch-chained and has from one to six carbon atoms, as illustrated by carbomethoxy, carbethoxy, carbo-n-propoxy, carbisopropoxy, carbo-n-butoxy, carbo-tert.-butoxy and carbo-n-hexoxy.

The compounds of formula I where Q is amino are useful both in the free base form and in the form of acid-addition salts; and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial cardiotonic properties inherent in the free base are not vitiated by side effects ascribable to the anions. In practicing the invention, it was found convenient to form the sulfate, phosphate, methanesulfonate or lactate. However, other appropriate pharmaceutically-acceptable salts within the scope of the invention are those derived from mineral acids such as hydrochloric acid and sulfamic acid; and organic acids such as acetic acid, citric acid, tartaric acid, ethanesulfonic acid, benzenesulfonic acid, p-toluenesulfonic acid, cyclohexylsulfamic acid, quinic acid, and the like, giving the hydrochloride, sulfamate, acetate, citrate, tartrate, ethanesulfonate, benzenesulfonate, p-toluenesulfonate, cyclohexylsulfamate and quinate, respectively.

The acid-addition salts of said basic compounds are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically-acceptable salts of said basic compounds are preferred, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a pharmaceutically-acceptable salt by ion exchange procedures.

The molecular structures of the composition aspects (1) of the invention were assigned on the basis of evidence provided by infrared, ultraviolet, nuclear magnetic resonance and mass spectra, by chromatographic mobilities, and, by the correspondence of calculated and found values for the elementary analyses for representative examples.

The manner of making and using the instant invention will now be generally described so as to enable a person skilled in the art of pharmaceutical chemistry to make and use the same, as follows:

The preparation of 1,2-dihydro-2-oxo-5-PY-nicotinamide (Ia) by reacting α-PY-β-($R_1R_2N$)acrolein (II) with malonamide is carried out preferably by mixing the reactants in a suitable solvent in the presence of a basic condensing agent. The reaction is conveniently run using a lower-alkanol as the solvent, preferably methanol or ethanol, and an alkali lower-alkoxide, preferably sodium methioxide or sodium ethoxide, respectively, as the basic condensing agent. In practicing the invention, the reaction was carried out in refluxing methanol using sodium methoxide. Other basic condensing agents include sodium hydride, lithium diethylamide, lithium diisopropylamide, and the like, in an aprotic solvent, e.g., tetrahydrofuran, acetonitrile, ether, benzene, dioxane, and the like.

The above-noted intermediate $\alpha$-PY-$\beta$-($R_1R_2N$)a-croleins (II) are generally known and are prepared by conventional methods. For example, II is produced by reacting an $\alpha$-PY-acetic acid with the reaction product obtained by reacting dimethylformamide with a phosphorus oxyhalide, preferably the oxychloride or oxybromide. The reaction of dimethylformamide with the phosphorus oxyhalide is run preferably below 10° C. and the resulting reaction product is heated with the $\alpha$-PY-acetic acid at about 50 to 80° C. to produce II. The intermediate $\alpha$-Py-acetic acids are generally known compounds which are prepared by conventional methods; for example, they are produced readily by heating the corresponding acetylpyridine of the formula PY-COCH$_3$ with sulfur and morpholine to produce the corresponding PY-thioacetomorpholinamide which on refluxing with 12n hydrochloric acid yields the $\alpha$-PY-acetic acid, e.g. $\alpha$-(3-ethyl-4-pyridinyl)acetic acid, is produced from 4-acetyl-3-ethylpyridine via 3-ethyl-4-pyridinylthioacetomorpholinamide [Jain et al., Indian Journal of Chemistry 10, 455 (1972)]. The acetylpyridines, i.e., PY COCH$_3$, also are generally known compounds which are prepared by conventional procedures, e.g., production from the corresponding cyanopyridines, i.e., PY-CN, [Reilly Tar & Chem. Corp. British Patent 920,303, published March 6, 1963; Case et al., J. Am. Chem. Soc. 78, 5842 (1956)].

The conversion of 1,2-dihydro-2-oxo-5-PY-nicotinamide (Ia) to 3-amino-5-PY-2(1H)-pyridinone (Ib) is carried out by reacting Ia with a reagent capable of converting carbamyl to amino. This reaction is conveniently run by heating an aqueous mixture containing an alkali metal hypohalite, preferably hypobromite or hypochlorite, and Ia, and then acidifying the reaction mixture, preferably with an aqueous mineral acid, e.g., hydrochloric acid. The reaction can be carried out from about 25° C. to 100° C., preferably about 60° C. to 100° C.

The reaction of $\alpha$-PY-$\beta$-($R_1R_2N$)acrolein (II) with $\alpha$-cyanoacetamide to produce 1,2-dihydro-2-oxo-5-PY-nicotino-nitrile (III) is carried out preferably by mixing the reactants in a suitable solvent in the presence of a basic condensing agent. The reaction is conveniently run using a lower-alkanol as a solvent, preferably methanol or ethanol, and an alkali lower-alkoxide, preferably sodium methoxide or sodium ethoxide, respectively, as the basic condensing agent. In practicing the invention, the reaction was carried out in refluxing methanol using sodium methoxide. Other basic condensing agents include sodium hydride, lithium diethylamide, lithium diisopropylamide, and the like, in an aprotic solvent e.g., tetrahydrofuran, acetonitrile, ether, benzene, dioxane, and the like.

The reaction of $\alpha$-PY-malonaldehyde (II') with $\alpha$-cyanoacetamide to produce 1,2-dihydro-2-oxo-5-PY-nicotino-nitrile (III) is carried out by heating the reactants in the presence of a catalytic condensing agent, preferably morpholine or piperidine and/or its acetate. The reaction is conveniently carried out by refluxing a benzene solution containing the reactants in the presence of morpholine, piperidine, morpholine acetate, piperidine acetate or mixtures thereof, preferably with a water separator attached to the reaction vessel to collect the water produced by the reaction.

The partial hydrolysis of 1,2-dihydro-2-oxo-5-PY-nicotinonitrile (III) to produce 1,2-dihydro-2-oxo-5-PY-nicotinamide (Ia) is carried out by heating III with concentrated sulfuric acid. While the reaction is conveniently and preferably run by heating the reactants on a steam bath, the temperature range for the reaction can vary from about 25° to 135° C. Alternatively, the conversion of III to Ia can be carried out by heating III at about 100° to 175° C. with polyphosphoric acid for about 1 to 5 hours.

The hydrolysis of 1,2-dihydro-2-oxo-5-PY-nicotinonitrile (III) to produce 1,2-dihydro-2-oxo-5-PY-nicotinic acid (IV) is conveniently run by heating III on a steam bath with an aqueous mineral acid, preferably 50% sulfuric acid.

The conversion of 1,2-dihydro-2-oxo-5-PY-nicotinic acid (IV) to 3-nitro-5-PY-2(1H)-pyridinone (Ic) is carried out by heating IV with a mixture of concentrated sulfuric acid and concentrated nitric acid. The heating of the reactants is conducted at about 60° to 100° C., preferably at about 70° to 90° C. Although it might be presumed that the nicotinic acid (IV) is first decarboxylated to produce the corresponding 3-unsubstituted-5-PY-2(1H)-pyridinone, which is then nitrated at the 3-position, it is noted, as shown above, that heating the corresponding nicotinonitrile (III) with concentrated sulfuric acid alone results in partial hydrolysis yielding the corresponding nicotinamide (Ia).

Alternatively, 1,2-dihydro-2-oxo-5-PY-nicotinonitrile (III) is readily converted step-wise to 3-nitro-5-PY-2(1H)-pyridinone (Ic) by first heating III with aqueous sulfuric acid for a longer period (supra) than required to form 1,2-dihydro-2-oxo-5-PY-nicotinic acid (IV) whereupon IV is first formed and then is decarboxylated on continued heating to produce 1,2-dihydro-2-oxo-5-PY-pyridine which is then nitrated under the same reaction conditions noted above for converting IV to Ic, that is, by heating 1,2-dihydro-2-oxo-5-PY-pyridine with a mixture of concentrated sulfuric acid and concentrated nitric acid to produce 3-nitro-5-PY-2(1H)-pyridinone (Ic).

The reaction of 3-nitro-5-PY-2(1H)-pyridinone (Ic) with a lower-alkylating agent to produce 1-R'-3-nitro-5-PY-2(1H)-pyridinone (Id) is generally carried out by reacting Ic with a lower-alkyl or a lower-hydroxyalkyl ester of a strong inorganic acid or an organic sulfonic acid, said ester having the formula R'-An, where An is an anion of a strong inorganic acid or an organic sulfonic acid, e.g., chloride, bromide, idodide, sulfate, methanesulfonate, benzenesulfonate, and para-toluenesulfonate (or tosylate), and R' is lower-alkyl or lower-hydroxyalkyl. This alkylation is preferably run using a slight excess of the alkylating agent although equimolar quantities give satisfactory results. The chloride, bromide, iodide or tosylate is preferred because of the ready availability of the requisite lower-alkyl halides or tosylates; and, the reaction is carried out preferably in the presence of an acid-acceptor. The acid-acceptor is a basic substance which preferably forms freely water-soluble by-products easily separable from the product of the reaction, including for example, sodium hydroxide, potassium hydroxide, sodium carbonate, potassium carbonate, sodium alkoxides, potassium alkoxides, sodium amide, and the like. The acid-acceptor picks up the hydrogen halide or tosylate (or HAn) which is split out during the course of the reaction. The reaction is preferably carried out in the presence of a suitable solvent which is inert under the reaction conditions. e.g., a solvent such as lower-alkanol, acetone, dioxane, dimethylformamide, dimethyl sulfoxide, hexamethyl phosphoramide, or a mixture of solvents, e.g., a mixture of water and a lower-alkanol. The reaction is generally carried out at a temperature between about room temperature (about 20°–25° C.) and 150° C., preferably heating on a steam bath in a stirred mixture of dimethylformamide and anhydrous potassium carbonate.

The reduction of 3-nitro-5-PY-2(1H)-pyridinone or 1-R'-3-nitro-5-PY-(1H)-pyridinone (Id) to produce 1-R-3-amino-5-PY-2(1H)-pyridinone (Ib) can be carried out either by catalytic or chemical reductive means. In practicing the invention, the hydrogenation of Ic or Id to produce Ib was conveniently run in a suitable solvent, e.g., dimethylformamide, in the presence of a hydrogenation catalyst, e.g., palladium-on-charcoal, at room temperature (about 20° 25° C.) until the uptake of hydrogen ceased. Other suitable solvents include tetrahydrofuran, dioxane, methanol, ethanol, water (containing a base, e.g., sodium hydroxide, potassium hydroxide, triethylamine, etc.), and the like. Other suitable hydrogenation catalysts include Raney nickel, platinum oxide, and the like. Chemical reducing agents useful in the reduction of Ic or Id to produce Ib include iron and acetic acid, zinc and hydrochloric acid, and the like.

The acylation of 1-R-3-amino-5-PY-2(1H)-pyridinone (Ib) to produce the corresponding 1-R-3-Q'NH-5-PY-2(1H)-pyridinone (Ie) is carried out by reacting Ib with a lower-alkanoylating agent or a lower-carbalkoxylating agent, e.g., a lower-alkanoyl halide, preferably chloride, a lower-alkanoic anhydride, a lower-alkyl haloformate, and the like, preferably in the presence of an acid-acceptor, as illustrated hereinabove for the lower-alkylation reaction. The lower-carbalkoxylation reaction can be carried out step-wise by first reacting the 1-R-3-amino-5-PY-1-R-2(1H)-pyridinone (Ib) with 1,1'-carbonyldiimidazole in the presence of a suitable solvent, e.g., dimethylformamide, to produce N-(1-R-1,2-dihydro-2-oxo-5-PY-3-pyridinyl)-imidazole-1-carboxamide which is then heated with a lower-alkanol to yield the corresponding lower-alkyl N-(1-R-1,2-dihydro-2-oxo-5-PY-3-pyridinyl)carbamate.

The following examples will further illustrate the invention without, however, limiting it thereto.

A.
1,2-DIHYDRO-2-OXO-5-(PYRIDINYL)-NICOTINONITRILES

A-1. 1,2-Dihydro-2-oxo-5-(4-pyridinyl)nicotinonitrile

A reaction mixture containing 35 g. of α-(4-pyridinyl)-β-dimethylaminoacrolein, 21.6 g. of sodium methoxide, 500 ml. of methanol and 17 g. of α-cyanoacetamide was heated to reflux with stirring whereupon an exothermic reaction ensued sufficient to cause the reaction mixture to reflux without the use of external heat. The reaction mixture was then refluxed with stirring for an additional thirty minutes, with solid precipitating after about five minutes of refluxing. The reaction mixture was cooled and the precipitate was collected, washed with ethyl ether and dried. The solid product was recrystallized from methanol and dried in vacuo at 80° C. to yield 13 g. of 1,2-dihydro-2-oxo-5-(4-pyridinyl)nicotinonitrile as its sodium salt, m.p. >300° C. Subsequent concentrations of the mother liquor yielded additional fractions of 10 g., 6.5 g. and 3 g. of the product, thereby resulting in a total of 32.5 g. of said sodium salt which is readily converted by treatment with hydrochloric acid as in Example A-2 to the corresponding N-H compound, that is, 1,2-dihydro-2-oxo-5-(4-pyridinyl)nicotinonitrile.

An alternative method of preparing 1,2-dihydro-2-oxo-5-(4-pyridinyl)nicotinonitrile is given as follows: A mixture containing 15 g. of α-(4-pyridyl)malonaldehyde, 9.3 g. of α-cyanoacetamide, 11 g. of morpholine, 13 g. of acetic acid and 1 liter of benzene was refluxed for about twenty-four hours with a water separator connected to the reaction vessel, then allowed to stand over the weekend. The solid which had separated was collected, recrystallized from dimethylformamide and dried in vacuo at 90° C. for about 15 hours to yield 5 g. of 1,2-dihydro-2-oxo-5-(4-pyridinyl)nicotinonitrile, m.p. >300° C.

A-2. 1,2-Dihydro-2-oxo-5-(3-pyridinyl)nicotinonitrile)

A mixture containing 93 g. of α-(3-pyridinyl)-β-dimethylaminoacrolein, 54 g. of α-cyanoacetamide, 65 g. of sodium methoxide and 900 ml. of methanol was refluxed with stirring for 2 hours and then allowed to stand at room temperature overnight. The resulting semi-solid cake was cooled and the solid was collected, washed with isopropyl alcohol and then ethyl ether and dried. The solid (sodium salt) was dissolved in water, the aqueous solution neutralized with 6N hydrochloric acid, and the acidic solution was cooled. The separated solid was collected, washed successively with isopropyl alcohol and ether and dried in vacuo at 80° C. to yield 41 g. of 1,2-dihydro-2-oxo-5-(3-pyridinyl)nicotinonitrile, m.p. > 300° C.

The above intermediate α-(3-pyridinyl)-β-dimethylaminoacrolein was prepared as follows: to 740 ml. of dimethylformamide kept below 10° C. was added dropwise with stirring 294 g. of phosphorus oxychloride and stirring was continued for another fifteen minutes then there was added 88 g. of α-(3-pyridinyl)acetic acid and the resulting reaction mixture was stirred at room temperature for one hour and then heated with stirring at about 70° C. for 2 hours and then cooled. The reaction mixture was then evaporated in vacuo to remove all of the volatile materials and the residue was added slowly to 1.24 liters of saturated potassium carbonate solution and 500 ml. of benzene with cooling. The mixture was allowed to stand overnight and then extracted with four portions of 50/50 (v/v) of benzene/ethanol. The combined extracts were dried over anhydrous potassium carbonate and evaporated in vacuo to remove the solvent and thereby yield 136 g. of dark oily material containing α-(3-pyridinyl)-β-dimethylacrolein.

A-3. 1,2-Dihydro-2-oxo-5-(2-pyridinyl)nicotinonitrile

A mixture containing 51 g. of α-(2-pyridinyl)-β-dimethylaminoacrolein, 24 g. of α-cyanoacetamide, 31 g. of sodium methoxide and 500 ml. of methanol was refluxed with stirring for 4 hours and then allowed to stand at room temperature overnight. The mixture was filtered and the filtrate evaporated in vacuo to remove the volatile materials. The residue was diluted with water and the mixture neutralized with 6N hydrochloric acid. The separated solid was collected, washed successively with water, ethanol and ether and then dried at 80° C. in vacuo to yield 18 g. of 1,2-dihydro-2-oxo-5-(2-pyridinyl)nicotinonitrile.

The above intermediate α-(2-pyridinyl)-β-dimethylamino-acrolein was prepared following the procedure described in Example A-2 using 50 g. of α-(2-pyridinyl)acetic acid hydrochloride, 336 ml. of dimethylformamide and 80 ml. of phosphorous oxychloride.

Following the procedure described in Example A-2 but using in place of place of α-(3-pyridinyl)-β-dimethylaminoacrolein a molar equivalent quantity of the appropriate α-PY-β-dimethylaminoacrolein, the 1,2-dihydro-2-oxo-5-PY-nicotinonitrile of Examples A-4 thru A-7 are obtained. The intermediate α-PY-β-dimethylaminoacroleins used in Examples A-4 thru A-7 are prepared by following the procedure described in the second paragraph of Example A-2 to produce α-(3-pyridinyl)-β-dimethylaminoacrolein but using in place of α-(3-pyridinyl)acetic acid a molar equivalent quantity of the appropriate α-PY-acetic acid.

A-4. 1,2-Dihydro-2-oxo-5-(2-methyl-3-pyridinyl)-nicotinonitrile using α-(2-methyl-3-pyridinyl)-β-dimethyl-aminoacrolein, in turn prepared from α-(2-methyl-3-pyridinyl)-acetic acid.

A-5. 1,2-Dihydro-2-oxo-5-(5-methyl-3-pyridinyl)-nicotinonitrile using α-(5-methyl-3-pyridinyl)-β-dimethyl-aminoacrolein, in turn prepared from α-(5-methyl-3-pyridinyl)-acetic acid.

A-6. 1,2-Dihydro-2-oxo-5-(3-ethyl-4-pyridinyl)-nicotinonitrile using α-(3-ethyl-4-pyridinyl)-β-dimethylaminoacrolein, in turn prepared from α-(3-ethyl-4-pyridinyl)-acetic acid.

A-7. 1,2-Dihydro-2-oxo-5-(4,6-dimethyl-2-pyridinyl)-nicotinonitrile using α-(4,6-dimethyl-2-pyridinyl)-β-dimethylaminoacrolein, in turn prepared from α-(4,6-dimethyl-2-pyridinyl)acetic acid.

B. 1,2-DIHYDRO-2-OXO-5-(PYRIDINYL)NICOTINIC ACIDS

B-1. 1,2-Dihydro-2-oxo-5-(4-pyridinyl)nicotinic acid

A mixture containing 227 g. of 1,2-dihydro-2-oxo-5-(4-pyridinyl)nicotinonitrile and 2.6 liters of 50% aqueous sulfuric acid was refluxed for five hours and then allowed to stand at room temperature overnight (about 15 hours).

The reaction mixture was then poured into 1 liter of water and the mixture cooled. The precipitate was collected, washed successively with water, ethanol and ether, and dried overnight in a vacuum oven at 80° C. to yield 206 g. of the crude product as a pink solid. A 40 g. portion of the crude product was mixed with water and the mixture neutralized by addition of potassium carbonate. The solid was collected, washed successively with water, methanol, and ether, and then recrystallized from dimethylformamide followed by successive washing with methanol and ether, and then drying in vacuo at 80° C. to yield, as a white solid, 27 g. of 1,2-dihydro-2-oxo-5-(4-pyridinyl)nicotinic acid, m.p. >300° C.

B-2. 1,2-Dihydro-2-oxo-5-(3-pyridinyl)nicotinic acid

A mixture containing 41 g. of 1,2-dihydro-2-oxo-5-(3-pyridinyl)nicotinonitrile and 410 ml. of 50% aqueous sulfuric acid was refluxed for 2 hours and then poured into 1.5 kg. of a mixture of ice and water. The acidic mixture was neutralized with 35% aqueous sodium hydroxide solution and the mixture cooled. The separated solid was collected, washed with water and dried in vacuo at 80° C. to yield 47 g. of 1,2-dihydro-2-oxo-5-(3-pyridinyl)nicotinic acid which was used directly without further purification in the next step described below as Example C-2.

B-3. 1,2-Dihydro-2-oxo-5-(2-pyridinyl)nicotinic acid, 14 g., was obtained following the procedure described in Example B2 using 18 g. of 1,2-Dihydro-2-oxo-5-(2-pyridinyl)-nicotinonitrile, 180 ml. of 50% aqueous sulfuric acid and a reflux period of four hours.

Following the procedure described in Example B-2 but using in place of 1,2-dihydro-2-oxo-5-(3-pyridinyl)-nicotinonitrile a molar equivalent quantity of a 1,2-dihydro-2-oxo-5-PY-nicotinonitrile, the corresponding 1,2-dihydro-2-oxo-5-PY-nicotinic acids of Examples B-4 thru B-7 are obtained.

B-4. 1,2-Dihydro-2-oxo-5-(2-methyl-3-pyridinyl)-nicotinic acid using 1,2-dihydro-2-oxo-5-(2-methyl-3-pyridinyl)-nicotinonitrile.

B-5. 1,2-Dihydro-2-oxo-5-(5-methyl-3-pyridinyl)-nicotinic acid using 1,2-dihydro-2-oxo-5-(5-methyl-3-pyridinyl)-nicotinonitrile.

B-6. 1,2-Dihydro-2-oxo-5-(3-ethyl-4-pyridinyl)-nicotinic acid using 1,2-dihydro-2-oxo-5-(3-ethyl-4-pyridinyl)-nicotinonitrile.

B-7. 1,2-Dihydro-2-oxo-5-(4,6-dimethyl-2-pyridinyl)-nicotinic acid using 1,2-dihydro-2-oxo-5-(4,6-dimethyl-2-pyridinyl)-nicotinonitrile.

C. 3-NITRO-5-(PYRIDINYL)-2(1H)-PYRIDINONES

C-1. 3-Nitro-5-(4-pyridinyl)-2(1H)-pyridinone To a stirred solution kept at 5°–10° C. and containing 154 g. of 1,2-dihydro-2-oxo-5-(4-pyridinyl)nicotinic acid in 450 ml. of concentrated sulfuric acid was added dropwise a solution containing 45 ml. of concentrated sulfuric acid and 160 ml. of 90% nitric acid. The reaction mixture was heated cautiously at 80° C. for 3 hours and then poured into 3.3 liters of a mixture of ice and water. The mixture was filtered and the precipitate washed with water. The combined filtrates were added slowly to one liter of 10% aqueous potassium carbonate soluton with stirring. The solution was neutralized by adding potassium carbonate and then made alkaline by adding 5% aqueous sodium bicarbonate solution. The precipitated product was collected, washed successively with a small amount of cold water, isopropyl alcohol and ether, and then dried in vacuo at 80° C. to yield 89 g. of the product. A 30 g. portion of the product was recrystallized from dimethylformamide to yield 20 g. of 3-nitro-5-(4-pyridinyl)-2(1H)-pyridinone, m.p. >300° C.

Alternatively, 3-nitro-5-(4-pyridinyl)-2(1H)-pyridinone is prepared step-wise starting with 1,2-dihydro-2-oxo-5-(4-pyridinyl)-nicotinonitrile as follows: A mixture containing 197 g. of 1,2-dihydro-2-oxo-5-(4-pyridinyl)-nicotinonitrile, 600 ml. of concentrated sulfuric acid and 150 liters of water was refluxed for 24 hours, cooled and poured into 10 liters of a mixture of ice and water. The mixture was neutralized with ammonium hydroxide and the separated precipitate was collected, washed with a small amount of cold water and dried in vacuo at 80° C. to yield 148 g. of 1,2-dihydro-2-oxo-5-(4-pyridinyl)-pyridine, m.p. 258°–260° C. An 80 g. portion of 1,2-dihydro-2-oxo-5-(4-pyridinyl)-pyridine was added to 288 ml. of concentrated sulfuric acid and the mixture heated to 70° C. To this stirred solution kept at 70°–80° C. was added dropwise a mixture containing 102 ml. of 90% nitric acid and 29 ml. of concentrated sulfuric acid. The reaction mixture was heated at about 80° C. for 3 hours after addition of the mixture of acids. The reaction mixture was then cooled and poured into a mixture of ice and water with stirring. The precipitate was collected and dried. It was then slurried with water and neutralized with 10% aqueous potassium bicarbonate solution. The precipitate was collected, washed with water and dried in vacuo at 80° C. to yield 56 g. of 3-nitro-5-(4-pyridinyl)-2(1H)-pyridinone.

Following the procedure described in the immediately preceding paragraph but starting with a molar equivalent quantity of the appropriate 1,2-dihydro-2-oxo-5-PY-nicotinonitrile in place of 1,2-dihydro-2-oxo-5-(4-pyridinyl)-nicotinonitrile, there are obtained first the following 1,2-dihydro-2-oxo-5-PY-pyridines; 1,2-dihydro-2-oxo-5-(3-pyridinyl)-pyridine; 1,2-dihydro-2-oxo-5-(2-pyridinyl)-pyridine; 1,2-dihydro-2-oxo-5-(2-methyl-3-pyridinyl)-pyridine; 1,2-dihydro-2-oxo-5-(5-methyl-3-pyridinyl)-pyridine; 1,2-dihydro-2-oxo-5-(3-ethyl-4-pyridinyl)-pyridine; and, 1,2-dihydro-2-oxo-5-(4,6-dimethyl-2-pyridinyl)-pyridine. In the subsequent second step, that is, the treatment of the appropriate 1,2-dihydro-2-oxo-5-PY-pyridine with concentrated sulfuric acid and concentrated nitric acid as above, there are obtained the corresponding respective 3-nitro compounds.

C-2. 3-Nitro-5-(3-pyridinyl)-2(1H)-pyridinone, 14 g., m.p. >300° C, was prepared following the procedure described in Example C-1 using 25 g. of 1,2-dihydro-2-oxo-5-(3-pyridinyl)nicotinic acid, 76.4 ml. of concentrated sulfuric acid, 26.6 ml. of 90% nitric acid and 7.6 ml. of concentrated sulfuric acid.

C-3. 3-Nitro-5-(2-pyridinyl)-2(1H)-pyridinone, 10 g., m.p. >300° C., was prepared following the procedure described in Example C-1 using 14 g. of 1,2-dihydro-2-oxo-5-(2-pyridinyl)nicotinic acid, 44 ml. of concentrated sulfuric acid, 15 ml. of 90% nitric acid and 4.4 ml. of concentrated sulfuric acid.

C-4. 1-Methyl-3-nitro-5-(4-pyridinyl)-2(1H)-pyridinone

A mixture containing 4.3 g. of 3-nitro-5-(4-pyridinyl)-2(1H)-pyridinone, 2.8 g. of anhydrous potassium carbonate and 40 ml. of dry dimethylformamide was stirred under nitrogen and heated on a steam bath for thirty minutes. The resulting fine suspension was cooled to room temperature and to it was added dropwise with stirring 3.7 g. of methyl tosylate. The resulting mixture was then stirred at room temperature for 18 hours, at steam bath temperature for 90 minutes, cooled and then poured onto ice. The separated solid was collected, washed well with water and dried at 60° C. and one-third atmosphere for eight hours. The resulting powder (3.2 g.) was crystallized from 50% aqueous ethanol to yield fine needles which were washed well with water and dried in vacuo for 3 hours at 100° C. and 10 mm. to yield 2.2 g. of 1-methyl-3-nitro-5-(4-pyridinyl)-2(1H)-pyridinone, m.p. 250°–252° C. In order to prove that the product obtained here was the N-methyl compound and not the O-methyl compound the following experiment was conducted: To 300 mg. of the product dissolved in 10 ml. of glacial acetic acid was added 2 ml. of 48% hydrogen bromide and the resulting clear solution was heated on a steam bath for about 75 minutes, cooled and the solvents distilled-off under reduced pressure. The residual yellow solid was triturated with dilute aqueous ammonium hydroxide solution, collected by filtration, washed with water and dried at 80° C. and one-third atmosphere for 20 hours to yield 0.30 g. of the starting material, m.p. 252°–254° C. Had the product been the O-methyl compound, that is, 2-methoxy-3-nitro-5-(4-pyridinyl)pyridine, the foregoing refluxing with hydrogen bromide in acetic acid would have produced the demethylated compound namely, 3-nitro-5-(4-pyridinyl)-2(1H)-pyridinone.

In another run following the above-described procedure there was obtained 11.2 g. of 1-methyl-3-nitro-5-(4-pyridinyl)-2(1H)-pyridinone, m.p. 151°–152° C., using 21.7 g. of 3-nitro-5-(4-pyridinyl)-2(1H)-pyridinone, 13.8 g. of anhydrous potassium carbonate, 300 ml. of dimethylformamide, 18.6 g. of methyl tosylate in 50 ml. of dimethylformamide added in one portion, and recrystallization from aqueous ethanol.

C-5. 1-Ethyl-3-nitro-5-(4-pyridinyl)-2(1H)-pyridinone

A mixture containing 21.7 g. of 3-nitro-5-(4-pyridinyl)-2(1H)-pyridinone, 13.8 g. of anhydrous potassium carbonate and 400 ml. of dry dimethylformamide was stirred at room temperature for 1 hour on a steam bath for 1 hour and then allowed to cool to room temperature. To the stirred yellow suspension was added a solution containing 20 g. of ethyl tosylate in 10 ml. of dimethylformamide and the resulting mixture was stirred at room temperature overnight (about 15 hours) and then on a steam bath for 90 minutes. The mixture was cooled and filtered. The filtrate was concentrated to near dryness under reduced pressure and 400 ml. of water was added. The yellow solid was collected by filtration, washed with water and dried at 50° C. in vacuo for 18 hours to yield 5.5 g. of pale yellow needles, m.p. 124°–126° C. (see below for recrystallization and identification). The filtrate was stored at 0° C. and the resulting yellow crystalline precipitate was collected and dried at 100° C. and 10 mm. for 4 hours to yield 8.0 g. of the product, 1-ethyl-3-nitro-5-(4-pyridinyl)-2(1H)-pyridinone, m.p. 175°–176° C. A sample of this product was recrystallized from 95% ethanol to produce the yellow crystalline 1-ethyl compound, m.p. 175°–176° C., whose nuclear magnetic resonance spectrum (10% in $CF_3COOD$) is consistent with the assigned N-ethyl structure. A portion of the above-noted pale yellow needles melting at 124°–126° C. was recrystallized from ethanol-water (3/1, v/v) to yield white needles, m.p. 126°–127° C., which was identified by its nuclear magnetic resonance spectrum (10% in $CF_3COOD$) as 2-ethoxy-3-nitro-5-(4-pyridinyl)pyridine.

Following the procedure described in Example C-1but using in place of 1,2-dihydro-2-oxo-5-(4-pyridinyl)-nicotinic acid a molar equivalent quantity of the appropriate 1,2-dihydro-2-oxo-5-PY-nicotinic acid, the corresponding 3-nitro-5-PY-2(1H)-pyridinones of Examples C-6 thru C-9 are obtained.

C-6. 3-Nitro-5-(2-methyl-3-pyridinyl)-2(1H)-pyridinone using 1,2-dihydro-2-oxo-5-(2-methyl-3-pyridinyl)-nicotinic acid.

C-7. 3-Nitro-5-(5-methyl-3-pyridinyl)-2(1H)-pyridinone using 1,2-dihydro-2-oxo-5-(5-methyl-3-pyridinyl)-nicotinic acid.

C-8. 3-Nitro-5-(3-ethyl-4-pyridinyl)-2(1H)-pyridinone using 1,2-dihydro-2-oxo-5-(3-ethyl-4-pyridinyl)-nicotinic acid.

C-9. 3-Nitro-5-(4,6-dimethyl-2-pyridinyl)-2(1H)-pyridinone using 1,2-dihydro-2-oxo-5-(4,6-dimethyl-2-pyridinyl)-nicotinic acid.

Following the procedure described in Example C-5 but using in place of ethyl tosylate a molar equiavlent quantity of the appropriate lower-alkyl tosylate or other lower-alkylating agents, the corresponding 1-(lower-alkyl)-3-nitro-5-PY-2(1H)-pyridinones of Examples C-10, C-11, C-12 and C-13 are obtained.

C-10. 3-Nitro-1-n-propyl-5-(4-pyridinyl)-2(1H)-pyridinone using 3-nitro-5-(4-pyridinyl)-2(1H)-pyridinone and n-propyl tosylate.

C-11. 1-Isobutyl-5-(2-methyl-3-pyridinyl)-3-nitro-2(1H)-pyridinone using 5-(2-methyl-3-pyridinyl)-3-nitro-2(1H)-pyridinone and isobutyl tosylate.

C-12. 1-n-Hexyl-3-nitro-5-(4-pyridinyl)-2(1H)-pyridinone using 3-nitro-5-(4-pyridinyl)-2(1H)-pyridinone and n-hexyl tosylate.

C-13. 1-(2-Hydroxyethyl)-3-nitro-5-(4-pyridinyl)-2(1H)-pyridinone using 3-nitro-5-(4-pyridinyl)-2(1H)-pyridinone and 2-hydroxyethyl tosylate.

D.
3-AMINO-5-(PYRIDINYL)-2-(1H)-PYRIDINONES
(From 3-nitro compounds)

D-1. 3-Amino-5-(4-pyridinyl)-2(1H)-pyridinone — A mixture containing 10 g. of 3-nitro-5-(4-pyridinyl)-2(1H)-pyridinone, 200 ml. of dimethylformamide and 1.5 g. of 10% palladium-on-charcoal was hydrogenated under pressure (50 p.s.i.) at room temperature until the uptake of hydrogen ceased (about 30 minutes). The reaction mixture was filtered through infusorial earth and the filtrate was heated in vacuo to remove the solvent. The residual material was crystallized from dimethylformamide, washed successively with ethanol and ether, and dried in a vacuum oven at 80° C. for 8 hours to yield 6 g. of 3-amino-5-(4-pyridinyl)-2(1H)-pyridinone, m.p. 294°–297° C. with decomposition.

The preparations of several acid-addition salts of 3-amino-5-(4-pyridinyl)-2(1H)-pyridinone are given in the following paragraphs.

Methanesulfonate — A 20 g. portion of 3-amino-5-(4-pyridinyl)-2(1H)-pyridinone was suspended in 250 ml. of warm methanol and methanesulfonic acid was added in a fine stream until the pH of the mixture dropped to about 2 to 3. The mixture was chilled and the separated orange solid was collected. The crystalline solid was recrystallized twice from aqueous methanol to yield, as golden crystals, 14 g. of 3-amino-5-(4-pyridinyl)-2(1H)-pyridinone methanesulfonate, m.p. 280°–282° C. with decomposition, after drying in vacuo at 80° C.

Sulfate — To a solution containing 10 g. of 3-amino-5-(4-pyridinyl)-2(1H)-pyridinone in about 250 ml. of aqueous methanol was added carefully concentrated sulfuric acid until the pH of the solution became 3. A yellow solid formed and the mixture was chilled. The separated solid was collected, recrystallized from water and dried at 80° C. and 0.11 mm. to yield 16.0 g. of 3-amino-5-(4-pyridinyl)-2(1H)-pyridinone sulfate, m.p. 287°–288° C. with decomposition.

Phosphate — A 10 g. portion of 3-amino-5-(4-pyridinyl)-2(1H)-pyridinone was dissolved in methanol-water and the solution made acidic by adding concentrated phosphoric acid to a pH of 2 and the mixture was stirred well and then allowed to stand over the weekend. The mixture was chilled; the separated solid was collected and washed successively with ethanol and ether, and then dried in vacuo at 70° C. to yield 4 g. of 3-amino-5-(4-pyridinyl)-2(1H)-pyridinone phosphate, m.p. 270°–272° C. with decomposition.

D-2. 3-Amino-5-(3-pyridinyl)-2(1H)-pyridinone — A mixture containing 14 g. of 3-nitro-5-(3-pyridinyl)-2(1H)-pyridinone, 300 ml. of dimethylformamide and 1.75 g. of 10% palladium-on-charcoal was hydrogenated under pressure (50 p.s.i.) at room temperature for 2 hours and then filtered. The solvent was distilled off in vacuo and the residue was slurried with isopropyl alcohol. The solid was collected by filtration and washed with ether and then dried. The solid was dissolved in dilute aqueous hydrochloric acid; the solution was treated with decolorizing charcoal and filtered; and, the filtrate was evaporated in vacuo. The residue was slurried with isopropyl alcohol; the solid collected by filtration, washed with ether and dried at 80° C. in vacuo to produce 11 g. of 3-amino-5-(3-pyridinyl)-2(1H)-pyridinone as its dihydrochloride, m.p. 280°–290° C. with decomposition.

D-3. 3-Amino-5-(2-pyridinyl)-2(1H)- pyridinone — A mixture containing 10 g. of 3-nitro-5-(2-pyridinyl)-2(1H)-pyridinone, 150 ml. of dimethylformamide and 1.5 g. of 10% palladium-on-charcoal was hydrogenated under pressure (50 p.s.i) at room temperature for 1 hour and filtered. The filter cake was washed with dimethylformamide. The combined filtrate and washings were evaporated in vacuo and the residual material was taken up in 6N aqueous hydrochloric acid. The acidic solution was evaporated in vacuo and the residue was recrystallized from dimethylformamide, washed successively with isopropyl alcohol and ether, and dried at 80° C. in vacuo to yield 2 g. of 3-amino-5-(2-pyridinyl)-2(1H)-pyridinone as its monohydrochloride, m.p. 259°–262° C. with decomposition.

D-4. 3-Amino-1-methyl-5-(4-pyridinyl)-2(1H)-pyridinone — A mixture containing 10.7 g. of 1-methyl-3-nitro-5-(4-pyridinyl)-2(1H)-pyridinione and 200 ml. of dimethylformamide was warmed to dissolve the nitro-pyridinone and the solution was filtered through infusorial earth. The filtrate was charged into a 500 ml. Parr bottle with 1.2 g. of 10% palladium-on-charcoal catalyst and the mixture was shaken under 40 p.s.i. of hydrogen at room temperature for 3hours, after which time no further hydrogen was taken up. The reaction mixture was filtered and the filtrate was concentrated to dryness under reduced pressure (0.1 mm.) on a water bath 40° C. leaving 10.1 g. of brown crystalline solid. The solid was recrystallized three times from benzene-ethanol, the third time using decolorizing charcoal, to yield 4.5 g. of 3-amino-1-methyl-5-(4-pyridinyl)-2(1H)-pyridinone, m.p. 175°–176° C. after drying at room temperature in vacuo for 20 hours.

D-5. 3-Amino-1-ethyl-5-(4-pyridinyl)-2(1H)-pyridinone — A solution containing 8.3 g. of 1-ethyl-3-nitro-5-(4-pyridinyl)-2(1H)- pyridinone in 200 ml. of ethyl acetate and 50 ml. of 95% ethanol was charged into a 500 ml. Parr bottle with 1.8 g. of 10% palladium-on-charcoal and the mixture was shaken under 42 p.s.i of hydrogen at room temperature for 50 minutes after which time no further hydrogen was taken up. The catalyst was filtered off and the solution was evaporated in vacuo to leave 7.5 g. of white crystalline solid. The solid was recrystallized from benzene to produce, as white needles, 5.8 g. of 3-amino-1-ethyl-5-(4-pyridinyl)-2(1H)-pyridinone, m.p. 181°–182° C. after drying at room temperature in vacuo for 50 hours and at 55° C. and 0.001 mm. for 5 hours.

Following the procedure described in Example D-4 but using in place of 1-methyl-3-nitro-5-(4-pyridinyl)-2(1H)-pyridinone a molar equivalent quantity of the appropriate 1-R-3-nitro-5-PY-2(1H)-pyridinone, the 1-R-3-amino-5-PY-2(1H)-pyridinones of Examples D-6 thru D-13 are obtained.

D-6. 3-Amino-1-n-propyl-5-(4-pyridinyl)-2(1H)-pyridinone using 1-n-propyl-3-nitro-5-(4-pyridinyl)-2(1H)-pyridinone.

D-7. 3-Amino-1-isobutyl-5-(4-pyridinyl)-2(1H)-pyridinone using 1-isobutyl-3-nitro-5-(4-pyridinyl)-2(1H)-pyridinone.

D-8. 3-Amino-1-n-hexyl-5-(4-pyridinyl)-2(1H)-pyridinone using 1-n-hexyl-3-nitro-5-(4-pyridinyl)-2(1H)-pyridinone.

D-9. 3-Amino-5-(2-methyl-3-pyridinyl)-2(1H)-pyridinone using 3-nitro-5-(2-methyl-3-pyridinyl)-2(1H)-pyridinone.

D-10. 3-Amino-5-(5-methyl-3-pyridinyl)-2(1H)-pyridinone using 3-nitro-5-(5-methyl-3-pyridinyl)-2(1H)-pyridinone.

D-11. 3-Amino-5-(3-ethyl-4-pyridinyl)-2(1H)-pyridinone using 3-nitro-5-(3-ethyl-4-pyridinyl)-2(1H)-pyridinine.

D-12. 3-Amino-5-(4,6-dimethyl-2-pyridinyl)-2(1H)-pyridinone. using 3-nitro-5-(4,6-dimethyl-2-pyridinyl)-2(1H)-pyridinone.

D-13. 3-Amino-1-(2-hydroxyethyl)-5-(4-pyridinyl)-2(1H)-pyridinone using 1-(2-hydroxyethyl)-3-nitro-5-(4-pyridinyl)-2(1H)-pyridinone.

E.
1,2-DIHYDRO-2-OXO-5-(PYRIDINYL)NICOTINAMIDES

E-1. 1,2-Dihydro-2-oxo-5-(4-pyridinyl)nicotinamide (optionally named 1,6-dihydro-6-oxo-[3,4'-bipyridin]-5-carboxamide) — A mixture containing 10 g. of 1,2-dihydro-2-oxo-5-(4-pyridinyl)nicotinonitrile and 100 ml. of 90% sulfuric acid was heated on a steam bath for 1 hour and then poured into ice. The acidic solution was neutralized with 35% aqueous sodium hydroxide solution and then made basic with 10% potassium bicarbonate solution. The separated product was collected, washed with water, dried, recrystallized from dimethylformamide, washed successively with ethanol and ethyl ether, and dried in vacuo at 80° C. to yield 8.5 g. of 1,2-dihydro-2-oxo-5-(4-pyridinyl)nicotinamide, m.p. >300° C.

In another run using 68 g. of 1,2-dihydro-2-oxo-4-(4-pyridinyl)nicotinonitrile, 700 ml. of 90% sulfuric acid, a heating period of 2 hours on a steam bath, isolation as above, recrystallization from dimethylformamide and washing with methanol and ether followed by drying, there was obtained a quantitative yield, 80 g. of the product, 1,2-dihydro-2-oxo-5-(4-pyridinyl)nicotinamide, m.p. 300° C.

E-2. 1,2-Dihydro-5-(4-pyridinyl)nicotinamide — A reaction mixture containing 17.6 g. of α-(4-pyridinyl)-β-dimethylaminoacrolein, 10.0 g. of malonamide, 10.8 g. of sodium methoxide and 200 ml. of methanol was refluxed for 30 minutes and allowed to cool. The separated product was collected and dried to yield "A". The mother liquor was concentrated in vacuo to remove the solvent and the residual material was diluted with water. The mixture was neutralized with acetic acid and the solid was collected, washed with water and dried to yield "B". "A" was dissolved in water and the solution was neutralized with acetic acid and the mixture cooled. The separated solid was collected, washed with water and dried. "A" and "B" were combined and recrystallized from 400 ml. of dimethylformamide to yield 13 g. of 1,2-dihydro-2-oxo-5-(4-pyridinyl)-nicotinamide, m.p. >300° C. The product obtained by this procedure was identical with the compound obtained in the immediately preceding Example E-1.

Following the procedure described in Example E-1 but using in place of 1,2-dihydro-2-oxo-5-(4-pyridinyl)-nicotinonitrile a molar equivalent quantity of the appropriate 1,2-dihydro-2-oxo-5-PY-nicotinonitrile, the 1,2-dihydro-2-oxo-5-PY-nicotinamides of Examples E-3 thru E-8 are obtained.

E-3. 1,2-Dihydro-2-oxo-5-(3-pyridinyl(nicotinamide using 1,2-dihydro-2-oxo-5-(3-pyridinyl)nicotinonitrile.

E-4. 1,2-Dihydro-2-oxo-5-(2-pyridinyl)nicotinamide using 1,2-dihydro-2-oxo-5-(2-pyridinyl)nicotinonitrile.

E-5. 1,2-Dihydro-2-oxo-5-(2-methyl-3-pyridinyl)-nicotinamide using 1,2-dihydro-2-oxo-5-(2-methyl-3-pyridinyl)-nicotinonitrile.

E-6. 1,2-Dihydro-2-oxo-5-(5-methyl-3-pyridinyl)-nicotinamide using 1,2-dihydro-2-oxo-5-(5-methyl-3-pyridinyl)-nicotinonitrile.

E-7. 1,2-Dihydro-2-oxo-5-(3-ethyl-4-pyridinyl)-nicotinamide using 1,2-dihydro-2-oxo-5-(3-ethyl-4-pyridinyl)-nicotinonitrile.

E-8. 1,2-Dihydro-2-oxo-5-(4,6-dimethyl-2-pyridinyl)-nicotinamide using 1,2-dihydro-2-oxo-5-(4,6-dimethyl-2-pyridinyl)-nicotinonitrile.

The products of E-3 thru E-8 also are produced by following the procedure described in Example E-2 using in place of α-(4-pyridinyl)-β-dimethylacrolein a molar equivalent quantity of the appropriate α-PY-β-dimethylacrolein, e.g., 1,2-dihydro-2-oxo-5-(3-pyridinyl)nicotinamide using α-(3-pyridinyl)-β-dimethylaminoacrolein, and the like.

F.
3-AMINO-5-(PYRIDINYL)-2(1H)-PYRIDINONES
(From 3-CONH₂ compounds)

F-1. 3-Amino-5-(4-pyridinyl)-2(1H)-pyridinone —To a solution containing 90 g. of sodium hydroxide in 1300 ml. of water kept at 0° C. was added dropwise with stirring 23 ml. of bromine. To the reaction mixture was then added 80 g. of 1,2-dihydro-2-oxo-5-(4-pyridinyl)nicotinamide and the resulting reaction mixture was heated on a steam bath for 3 hours. The reaction mixture was cooled to room temperature, acidified slowly with 6N hydrochloric acid and the resulting acidic mixture was stirred for an additional 30 minutes. The acidic mixture was neutralized with 10% aqueous potassium bicarbonate solution and the mixture cooled. The precipitate was collected, washed with water and dried. The solid product was recrystallized from dimethylformamide, washed successively with methanol and ethyl ether and dried in vacuo at 80° C. to yield 35 g. of 3-amino-5-(4-pyridinyl)-2(1H)-pyridinone, m.p. 295°–297° C. with decomposition. Another 7 g. of the product was obtained by diluting the mother liquor with ethyl ether.

Following the procedure described in Example F-1 but using in place of 1,2-dihydro-2-oxo-5-(4-pyridinyl)-nicotinamide a molar equivalent quantity of the appropriate 1,2-dihydro-2-oxo-5-PY-nicotinamide, the 3-amino-5-PY-2(1H)-pyridinones of Examples F-2 thru F-7 are obtained.

F-2. 3-Amino-5-(3-pyridinyl)-2(1H)-pyridinone using 1,2-dihydro-2-oxo-5-(3-pyridinyl)nicotinamide.

F-3. 3-Amino-5-(2-pyridinyl)-2(1H)-pyridinone using 1,2-dihydro-2-oxo-5-(2-pyridinyl)nicotinamide.

F-4. 3-Amino-5-(2-methyl-3-pyridinyl)-2(1H)-pyridinone using 1,2-dihydro-2-oxo-5-(2-methyl-3-pyridinyl)nicotinamide.

F-5. 3-Amino-5-(5-methyl-3-pyridinyl)-2(1H)-pyridinone using 1,2-dihydro-2-oxo-5-(5-methyl-3-pyridinyl)nicotinamide.

F-6. 3-Amino-5-(3-ethyl-4-pyridinyl)-2(1H)-pyridinone using 1,2-dihydro-2-oxo-5-(3-ethyl-4-pyridinyl)-nicotinamide.

F-7. 3-Amino-5-(4,6-dimethyl-2-pyridinyl)-2(1H)-pyridinone using 1,2-dihydro-2-oxo-5-(4,6-dimethyl-2-pyridinyl)nicotinamide.

G.
1,2-DIHYDRO-3-(ACYLAMIDO)-5-(PYRIDINYL)-2(1H)-PYRIDINONES

G-1. N-[1,2-Dihydro-2-oxo-5-(4-pyridinyl)-3-pyridinyl]acetamide — A mixture containing 9.4 g. of 3-amino-5-(4-pyridinyl)-2(1H)-pyridinone, 5.6 g. of acetic anhydride and 120 ml. of pyridine was heated on a steam bath for 1 hour and then allowed to cool. The separated product was collected, washed with ether and dried, and recrystallized twice from dimethylformamide to yield 8 g. of N-[1,2-dihydro-2-oxo-5-(4-pyridinyl)-3-pyridinyl]acetamide, m.p. >300° C.

G-2. Methyl N-[1,2-dihydro-2-oxo-5-(4-pyridinyl)-3-pyridinyl]carbamate — A mixture containing 10 g. of 3-amino-5-(4-pyridinyl)-2(1H)-pyridinone, 100 ml. of dimethylformamide and 24 g. of 1,1'-carbonyldiimidazole was stirred at room temperature for 2 hours and the solvent then distilled off in vacuo. Cold water was added to the residue and the mixture was stirred until the evolution of carbon dioxide stopped. The solid was collected, washed with water and dried. The solid was next slurried with acetone, collected and dried. The solid was dissolved in 200 ml. of dimethylformamide, the solution treated with decolorizing charcoal and the mixture filtered. The filtrate was heated in vacuo to remove the dimethylformamide. The remaining material, which consisted primarily of N-[1,2-dihydro-2-oxo-5-(4-pyridinyl)-3-pyridinyl]-imidazole-1-carboxamide, was heated with methanol whereupon a reaction ensued. The reaction mixture was allowed to cool and the separated product was collected and dried to yield 3.5 g. of methyl N-[1,2-dihydro-2-oxo-5-(4-pyridinyl)-3-pyridinyl]carbamate, m.p. >300° C.

Following the procedure described in Example G-1 but using in place of acetic anhydride a molar equivalent quantity of the appropriate acylating agent, the compounds of Examples G-3 thru G-5 are obtained.

G-3. N-[1,2-Dihydro-2-oxo-5-(4-pyridinyl)-3-pyridinyl]propionamide using propionic anhydride.

G-4. N-[1,2-Dihydro-2-oxo-5-(4-pyridinyl)-3-pyridinyl]isobutyramide using isobutyric anhydride.

G-5. N-[1,2-Dihydro-2-oxo-5-(4-pyridinyl)-3-pyridinyl]caproamide using caproic anhydride.

Following the procedure described in Example G-2 but first using in place of 3-amino-5-(4-pyridinyl)-2(1H)-pyridinone a corresponding molar equivalent quantity of the appropriate 3-amino-5-PY-2(1H)-pyridinone to produce the corresponding N-(1,2-dihydro-2-oxo-5-PY-3-pyridinyl)-imidazole-1-carboxamide and then reacting said imidazole-1-carboxamide with the appropriate alkanol in place of methanol, there are obtained the corresponding lower-alkyl N-(1,2-dihydro-2-oxo-5-PY-3-pyridinyl)carbamates of Examples G-6 thru G-8.

G-6. Ethyl N-[1,2-dihydro-2-oxo-5-(4-pyridinyl)-3-pyridinyl]carbamate first using 3-amino-5-(4-pyridinyl)-2(1H)-pyridinone and the using ethanol.

G-7. n-Hexyl N-[1,2-dihydro-2-oxo-5-(4-pyridinyl)-3-pyridinyl]carbamate using 3-amino-5-(4-pyridinyl)-2(1H)-pyridinone and then reacting the resulting N-[1,2-dihydro-2-oxo-5-(4-pyridinyl)-3-pyridinyl]-imidazole-1-carboxamide with n-hexanol.

G-8. Isobutyl N-[1,2-dihydro-2-oxo-5(4-pyridinyl)-3-pyridinyl]carbamate first using 3-amino-5-(4-pyridinyl)-2(1H)-pyridinone and then reacting the resulting N-[1,2-dihydro-2-oxo-5-(4-pyridinyl)-3-pyridinyl]-1-imidazole-1-carboxamide with isobutyl alcohol.

The usefulness of the compounds of formula I where Q is amino (preferred), NHAc, hydrogen or cyano as cardiotonic agents is demonstrated by their effectiveness in standard pharamacological test procedures, for examples, in causing a significant increase in the contractile force of the isolated cat atria and papillary muscle and in causing a significant increase in the cardiac contractile force in the anesthetized dog with low or minimal changes in heart rate and blood pressure. These test procedures are described in the following paragraphs.

Isolated Cat Atria and Papillary Muscle Procedure

Cats of both sexes, weighing 1.5 to 3.5 kg. are each anesthetized with 30 mg./kg. i.p. of sodium pentobarbital and exsanguinated. The chest of each cat is opened, the heart excised, rinsed with saline, and the two atria and one or more small, thin papillary muscles from the right ventricle are dissected. The tissues are then transferred to a Petri dish filled with cold modified Tyrode's solution and bubbled with $O_2$. A silver wire is attached to each of two opposite ends of the tissue and one of the wires is hooked to a glass electrode. The preparation is then immediately mounted in a 40 or 50 ml. organ bath filled with modified Tyrode's solution at 37° C. The second wire is attached to a force-displacement transducer and the tension is adjusted to obtain a maximum contractile force (papillary muscle 1.5±0.5 g., left atria 3.0±0.6 g. right atria 4.5±0.8 g.). The transducer is connected to a Grass polygraph and the force and rate of contraction is recorded continuously. The right atrium is beating spontaneously due to the presence of the sino-atrial node, while the left atrium and the papillary muscle are stimulated electrically at a rate of 2 beats/sec. by a suprathreshold rectangular pulse of 0.5 millisecond duration.

The modified Tyrode's solution bathing the preparation is of the following composition (in millimoles): NaCl 136.87, KCl 5.36, $NaH_2PO_4$ 0.41, $CaCl_2$ 1.8, $MgCl_2 \cdot 6H_2O$ 1.05, $NaHCO_3$ 11.9, glucose 5.55 and EDTA 0.04. The solution is equilibrated with a gas mixture consisting of 95% $O_2$ and 5% $CO_2$ and the pH is adjusted to 7.4 with dilute solution of sodium bicarbonate.

The preparation is left to equilibrate for 1 hour before any compound is administered, and the bathing fluid is changed 3 to 4 times during the equilibration time. The compound dissolved in a vehicle (e.g., Tyrode's solution or aqueous solution of acid-additon salt of compound tested) or the vehicle alone is added to the tissue bath and the full response is recorded. The tissues are washed between doses until pre-drug control values of rate and force of contraction are obtained. Four to six doses are given to the same preparation over a period of 4 to 6 hours.

When tested by the above-described Isolated Cat Atria and Papillary Muscle Procedure, the compounds of formula I where Q is amino, NHAc, hydrogen or cyano, when tested at doses of 3 to 100 µg./ml., were found to cause significant increase, that is, greater than 25%, in papillary muscle force and a significant increase, that is, greater than 25%, in right atrial force, while causing only a low percentage increase (about one-third or less than the percentage increase in right atrial or papillary muscle force) in right atrial rate.

Anesthetized Dog Procedure

Mongrel dogs of both sexes weighing 9–15 kg. are used in this procedure. The dogs are each anesthetized with 30 mg./kg. i.v. sodium pentobarbital. Supplemental doses of pentobarbital are administered whenever necessary. An intra-tracheal cannual is inserted and ventilation is carried out by means of a Harvard constant-volume, positive pressure pump using room air. The right femoral artery is cannulated and the cannula is attached to a Statham P23A pressure transducer for the measurement of arterial blood pressure. The right femoral vein is cannulated and used for intravenous administration of compounds to be tested. Pin electrodes are attached to the right forelimb, right hindlimb and left hindlimb, and lead II electrocardiogram is monitored.

A ventro-dorsal incision at the third inter-costal space is made, the heart is exposed and a Walton-Brodie strain gauge is sutured to the wall of the right ventricle for the measurement of cardiac contractile force, that is, cardiac contractility. Aortic and coronary blood flow are measured with a pulsed field electromagnetic flow probe (Carolina Medical Electronics) inserted around the blood vessel in question. Aortic blood flow is used as an approximate index of cardiac output and total peripheral resistence is calculated from aortic flow and mean arterial pressure. All the above parameters measured are recorded simultaneously on a multichannel Grass polygraph.

A given compound is infused into the femoral vein at a rate from 0.03 to 0.10 mg./kg./minute until a maximum inotropic effect is obtained. The infusion of the compound is then continued for ten more minutes to maintain an equilibrium at this maximal inotropic effect. At the end of the equilibrium time the infusion is stopped and the rate of decline in cardiac contractile force is observed. Alternatively, the compound is administered intravenously as a single bolus injection of 0.30 to 30 mg./kg.

When tested by the above-described Anesthetized Dog Procedure, the compound of formula I where Q is amino (preferred), NHAc, hydrogen or cyano, when administered intraveneously at a rate of about 0.03 to 0.10 mg./kg./min. or as a single bolus injection of 0.30 to 30 mg./kg. caused a significant increase, that is, greater than 25%, in cardiac contractile force or cardiac contractility with only low or minimal changes (less than 25%) in heart rate and blood pressure.

The actual determination of the numerical cardiotonic data definitive for a particular compound of the invention is readily obtained according to the above-described standard test procedures by technicians versed in pharmacological test procedures, without any need for any extensive experimentation.

Preferred embodiments are subjected to further standard test procedures. For example, 3-amino-5-(4-pyridinyl)-2(1H)-pyridinone, a particularly preferred embodiment, when tested orally in the unanesthetized dog at a dose of 1.9, 3.8, 7.5 or 10 mg./kg. was found to cause, respectively, a 39, 44, 47 or 98% increase in cardiac contractile force with a duration of action of more than three hours; no significant changes in blood pressure were observed with these doses and a significant increase in heart rate was observed only at the highest dose of 10 mg./kg. p.o.

The present invention includes within its scope a cardiotonic composition for increasing cardiac contractility, said composition comprising a pharmaceutically-acceptable carrier and, as the active component thereof, a cardiotonic 1-R-3-Q-5-PY-2(1H)-pyridinone of formula I where Q is amino (preferred), NHAc, hydrogen or cyano, or pharmaceutically-acceptable acid-addition salt thereof where Q is amino. The invention also includes within its scope the method for increasing cardiac contractility in a patient requiring such teatment which comprises administering to such patient an effective amount of said 1-R-3-Q-5-PY-2(1H)-pyridinone of formula I where Q is amino (preferred), NHAc, hydrogen or cyano, or pharmaceutically-acceptable acid-addition salt thereof where Q is amino. In clinical practice the said compounds of formula I will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These commpositions may also contain additional substances other than inert diluents, e.g., lubricating agents, such as magnesium stearate talc and the like.

Liquid compositions for oral administration include pharmaceutically-acceptable emulsions, solutions, suspensions, syrups and elixers containing inert diluents commonly used in the art, such as water and liquid paraffin. Besides inert diluents such compositions may also contain adjuvants, such as wetting and suspending agents, and sweetening, flavouring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions may also contain adjuvants such as stabilising, preserving, wetting, emulsifying and dispersing agents.

They may be sterilized, for example by filtration through a bacteria-retaining filter, by incorporation of sterilising agents in the compositions, by irradiation or by heating. They may also be manufactured in the form of sterile solid compositions which can be dissolved in sterile water or some other sterile injectable medium immediately before use.

The percentage of active component in the said composition and method for increasing cardiac contractility may be varied so that a suitable dosage is obtained. The dosage administered to a particular patient is variable, depending upon the clinician's judgement using as the criteria: the route of administation, the duration of treatment, the size and condition of the patient, the potency of the active component and the patient[s response thereto. An effective dosage amount of active component can thus only be determined by the clinician considering all criteria and utilizing his best judgement on the patient's behalf.

We claim:

1. A 1-R-3-Q-5-PY-2(1H)-pyridinone having the formula

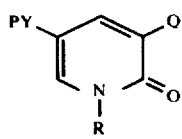

where PY is 4- or 3- or 2-pyridinyl or 4- or 3- or 2-pyridinyl having one or two lower-alkyl substituents, R is hydrogen, lower-alkyl or lower-hydroxyalkyl having from two to six carbon atoms and having its hydroxy group and free valence bond on different carbon atoms an Q is cyano.

2. A compound according to claim 1 where R is hydrogen and Q is cyano.

3. 1,2-Dihydro-2-oxo-5-(4-pyridinyl)nicotinonitrile according to claim 2.

4. A cardiotonic composition for increasing cardiac contractility, said composition comprising a pharmaceutically-acceptable inert carrier and, as the active component thereof, an effective amount of a cardiotonic 1-R-3-Q-5-PY-2(1H)-pyridinone having the formula

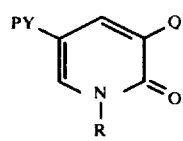

where PY is 4- or 3- or 2-pyridinyl or 4- or 3- or 2-pyridinyl having one or two lower-alkyl substituents, R is hydrogen, lower-alkyl or lower-hydroxyalkyl having from two to six carbon atoms and having its hydroxy group and free valence bond on different carbon atoms Q is cyano.

5. The method for increasing cardiac contractility in a patient requiring such treatment which comprises administering to such patient an effective amount of a cardiotonic 1-R-3-Q-5-PY-2(1H)-pyridinone having the formula

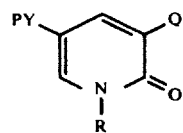

where PY is 4- or 3- or 2-pyridinyl or 4- or 3- or 2-pyridinyl having one or two lower-alkyl substituents, R is hydrogen, lower-alkyl or lower-hydroxyalkyl having from two to six carbon atoms and having its hydroxy group and free valence bond on different carbon atoms and Q is cyano.

* * * * *

UNITED STATES PATENT AND TRADEMARK OFFICE
CERTIFICATE OF CORRECTION

PATENT NO. : 4,004,012
DATED : January 18, 1977
INVENTOR(S) : George Y. Lesher and Chester J. Opalka, Jr.

It is certified that error appears in the above-identified patent and that said Letters Patent are hereby corrected as shown below:

Column 4, Formula II should read:

Column 7, line 20, "12n" should read -- 12N --.

Column 7, line 25, "PY COCH$_3$" should read -- PY-COCH$_3$ --.

Column 9, line 18, "20°25°C." should read -- 20° to 25°C. --.

Column 24, line 22, before "Q" insert -- and --.

Signed and Sealed this

Twenty-fourth Day of May 1977

[SEAL]

Attest:

RUTH C. MASON
*Attesting Officer*

C. MARSHALL DANN
*Commissioner of Patents and Trademarks*